United States Patent [19]

Tilley et al.

[11] Patent Number: 5,087,719
[45] Date of Patent: Feb. 11, 1992

[54] DEHYDROGENATIVE POLYMERIZATION OF SILANES TO POLYSILANES BY CATALYSTS OF TRANSITION-METAL SILYL DERIVATIVES

[75] Inventors: T. Don Tilley, San Diego, Calif.; Hee-Gweon Woo, Cambridge, Mass.

[73] Assignee: The United States of America as represented by the Secretary of the Air Force, Washington, D.C.

[21] Appl. No.: 589,704

[22] Filed: Sep. 27, 1990

[51] Int. Cl.$^5$ ............................................. C07F 7/08
[52] U.S. Cl. .................................................... 556/430
[58] Field of Search ............................................ 556/430

[56] References Cited

U.S. PATENT DOCUMENTS

| | | | |
|---|---|---|---|
| 4,276,424 | 6/1981 | Peterson, Jr. et al. | 556/430 |
| 4,611,035 | 9/1986 | Brown-Wensley et al. | 556/430 X |
| 4,704,444 | 11/1987 | Brown-Wensley et al. | 528/25 |
| 4,780,337 | 10/1988 | Seyferth et al. | 427/387 |
| 4,808,685 | 2/1989 | Bortolin | 528/14 |
| 4,820,783 | 4/1989 | Seyferth et al. | 525/474 |
| 4,965,386 | 10/1990 | Watson et al. | 556/430 |

*Primary Examiner*—Paul F. Shaver
*Attorney, Agent, or Firm*—Thomas C. Stover; Donald J. Singer

[57] ABSTRACT

A mechanism for the dehydrogenative polymerization of silanes to polysilanes is proposed, based on studies with zirconocene and hafnocene catalysts. This is a new polymerization mechanism, based on metal-mediated step-growth of the polymer. Key features of the mechanism are: 1) Coordinatively unsaturated metal hydride species appear to be the active catalysts. 2) Other intermediates are polysilyl metal complexes $M(SiHR)_nH$ and free polysilanes. 3) The proposed mechanism involves two types of $\sigma$-bond methathesis reactions that proceed via four-center transition states. This proposal of a mechanism is based on model reactions and observation of intermediates. Chemistry relevant to the polymerization process suggests that silyl groups readily participate in $\sigma$-bond methathesis reactions with $d^0$ metal centers via four-center transition states.

8 Claims, No Drawings

DEHYDROGENATIVE POLYMERIZATION OF SILANES TO POLYSILANES BY CATALYSTS OF TRANSITION-METAL SILYL DERIVATIVES

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to dehydrogenative polymerization of silanes to polysilanes, particularly by employing catalysts of transition-metal silyl derivatives therefor.

2. The Prior Art

Recently polysilane polymers -(SiRR')x-, have attracted a great deal of attention because of the development of various technological applications. Some polysilanes, on thermal treatment, yield polycarbosilanes that can be spun into fibers and converted to SiC fibers having high tensile strength and oxidation resistance. Such SiC fibers are capable of reinforcing ceramic materials. Polysilanes also possess remarkable electronicpproperties that allow them to be used as dopable semiconductors, photoinitiators in olefin polymerization, photoresists, photoconductors, and non-linear optical materials.

These applications have been made possible by the development of polysilane syntheses based on the Wurtz-type coupling reaction of appropriate dichlorosilanes with an alkali metal in an inert solvent. This synthetic method is the only useful route to polysilanes and has served well to allow the above applications to evolve. Use of the Wurtz-type coupling method suffers from a number of inherent difficulties including poor control of polymer molecular weight, the production of large quantities of NaCl side product, and the dangers of handling large quantities of molten alkali metals. Wider application of polysilane polymers was therefore hampered by the need for new polymerization reactions.

Then Harrod and others reported that titanocene and zirconocene alkyl derivatives are active catalysts for the dehydrogenative coupling of primary silanes $RSiH_3$ to linear polysilanes with ca. 10-20 Si atoms eg:

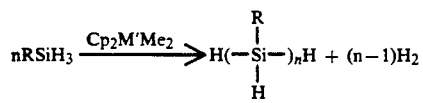

wherein as used above and below, Me is methyl, R is Phenyl, Alkyl, M' is Ti, Zr and Cp is $\eta^5$-$C_5H_5$. See Woo, H. G.; Tilley, T. D., *J. Am. Chem. Soc.* 1989, 111, 8043-44, particularly footnote 2, incorporated herein by reference.

The above catalysts are referred to herein as the M-C bonded species (metal-carbon) while the invention, described below, is referred to as the M-Si bonded species (metal-silicon).

However in the Harrod systems, above, polymerization times are relatively slow, requiring up to several days for the alkyl-based (M-C) catalyst and the degrees of polymerization of such polysilanes are limited to about 20.

Accordingly there is a need and market for an improved process of catalytic polymerization of silanes that overcomes the above prior art shortcomings.

There has now been discovered a method for the improved polymerization of silanes to polysilanes that employs catalysts of M-Si bonded species in which the polymerization reaction is carried out within minutes rather than days and which produces polysilanes with degrees of polymerization up to 70-85 or more.

SUMMARY OF THE INVENTION

Broadly the present invention provides a method for catalytic dehydrogenative silane polymerization comprising, adding metal silyl catalyst precursors to silanes in a hydrocarbon solution to obtain polysilanes.

Included in such catalyst precursors are silyl complexes of the type $Cp'_2 M(SiR_3)R'$ wherein $Cp=\eta^5$-$C_5H_5$, $Cp'=Cp$, $Cp^*$; $Cp^*=\eta^5$-$C_5Me_5$; Me=methyl; M=Zr, Hf; R=Me, Ph, $SiMe_3$ and R'=Cl, alkyl, silyl to obtain polysilanes.

DESCRIPTION OF PREFERRED EMBODIMENTS

It has been found that in the catalytic dehydrogenative coupling (polymerization of) silanes, catalysts of M-Si bonded species, undergo initiation reactions much faster than catalysts of M-C bonded species, particularly with early transition-metal silyl derivatives.

More particularly it has been found that a number of zirconium and hafnium silyl complexes of the type $Cp'_2M(SiR_3)R'$ are catalyst precursors for this dehydrogenative coupling reaction and that polymer molecular weights can vary as a function of reaction conditions and catalyst.

The following discussion suggests a mechanism for dehydrogenative silane polymerization by early transition-metal silyl derivatives, eg. zirconocene and hafnocene catalysts, which mechanism applies as well to titanium silyl derivatives and tantalum silyl derivatives.

Investigations of $d^0$ metal-silicon bond reactivity have revealed a number of process that can be described as "$\sigma$-bond methathis" reactions involving M-H, M-Si, Si-H, Si-Si and H-H bonds. Similar reactions for $d^0$ M-C and M-H bonds have been described, and mechanistic studies indicate that they pass through concerted, four-center transition states. See Woo, H. G.; and Tilley, T. D.; *J. Am. Chem. Soc.* 1989, 111, 8043-44, particularly footnote 4, incorporated herein by reference.

Observation of the six unique processes represented by the 4 equations in Scheme 1 below, suggests that silicon readily participates in $\sigma$-bond methathesis reactions with $d^0$ metal centers via four-center transition states A-D. These processes have been observed for zirconocene and hafnocene derivatives that are catalysts for the dehydrogenative coupling of silanes.

The forward reaction represented by eq (a), M-Si bond hydrogenolysis, has previously been reported for $Cp_2Zr(SiR_3)Cl$ complexes and appears to be generally facile for $d^0$ silyl complexes. (Campion, B. K.; Tilley, T. D. et al. *J. Am. Chem Soc.* 1987, 109, 2049; and Roddick, D. M.; Tilley, T. D. et al., *Organometallics* 1989, 8, 324 incorporated herein by reference. The reverse, M-Si bond-forming process is observed in reactions between hydrides $CpCp^*MHCl$ (1, M=Zr; 2, M=Hf) and $PhSiH_3$ to produce $CpCp^*M(SiH_2Ph)Cl$(3, M=Zr; M=Hf) and $H_2$. See Woo, H. G.; Tilley, T. D. *J. Am. Chem. Soc.* 1989, 111, 3757, incorporated herein by reference. Hydrogen/deuterium exchange, possibly via transition state B, occurs rapidly between 1 or 2 and PhSiD$_3$.

Scheme I. Possible σ-Bond Metathesis Processes Involving a d$^O$ Metal Center, Hydrogen, and one or two Silyl Groups

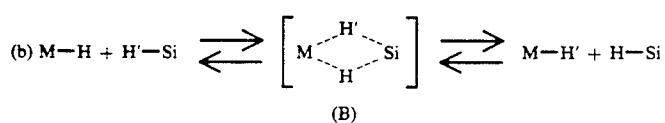

(A)

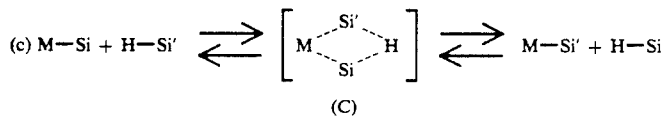

(B)

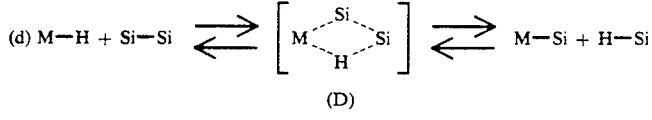

(C)

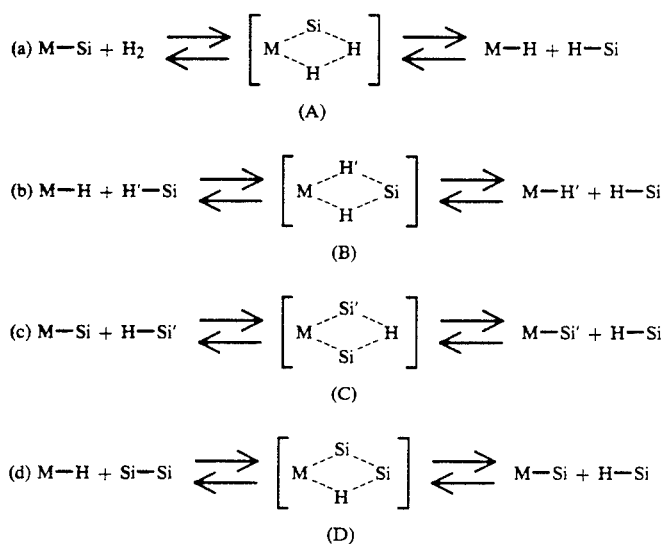

(D)

Scheme II. Proposed Mechanism for Dehydrogenative Silane Polymerization by Zirconocene and Hafnocene Catalysts

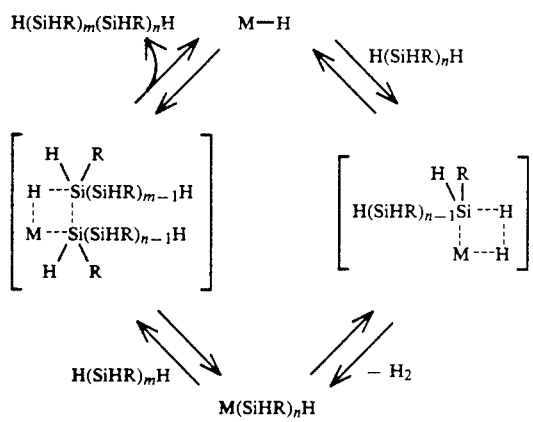

The σ-bond metathesis chemistry summarized above suggests a mechanism for the dehydrogenative polymerization of silanes by zirconocene and hafnocene derivates (Scheme II above). A coordinatively unsaturated hydride complex is implicated as an important intermediate, since Si-Si bond formation results in production of metal hydride species, and since hydride complexes themselves are active catalysts. Such hydride species are readily formed in solution from catalyst precursors via σ-bond methathesis reactions (see Scheme I). Each catalytic cycle involves formation of a metal silyl derivative and free polysilane. Observed steric constraints on these σ-bond methathesis reactions suggest that the metal hydride interacts predominantly with the sterically less crowded —SiH$_2$R end group of a polymer chain, giving linear chain growth. It is also believed that steric constraints are such that one of the reacting silanes in a cycle must be primary (n or m=1),
resulting in chain growths of only one Si per cycle. Note that the mechanism proposed here involves reactions at only one M-X σ-bond, whereas a metal silylene-based mechanism (per footnote 2, cited above) requires that two σ-bonds be used. The results are consistent with involvement of only one σ-bond, since compounds 3 and 4 above, are catalyst precursors for the polymerization of PhSiH$_3$, which quantitatively converts these chloro complexes to the corresponding hydrides CpCp*MHCl. See Woo, H. G.; Tilley, T. D., J. Am. Chem. Soc. 1989, 111, 8043-44, incorporated herein by reference.

The following examples are intended as an illustration of the methods of the invention and should not be construed in limitation thereof.

EXAMPLE I

Using model reactions, certain intermediates for the proposed mechanism were detected. Thus CpCp*Hf(SiHPhSiH$_2$Ph)Cl (6), prepared independently from 1 and PhH$_2$SiSiH$_2$Ph and isolated as a 1:1 mixture of two diastereomers, was identified (by $^1$H NMR spectroscopy) in the slow oligomerization of PhSiH$_3$ by 4. Addition of 2 equivalents of PhSiH$_3$ to 4 resulted in formation of 2, 6, disilane and trisilane after 24 hr. (33% conversion) as given below. For further discussion see Woo, H. G.; Tilley, T. D., J. Am. Chem. Soc. 1989, 111, 8043-44, particularly footnotes 7 and 8, incorporated herein by reference.

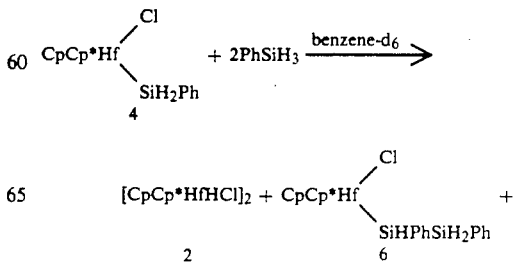

-continued

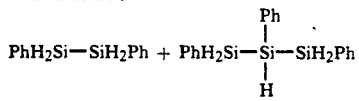

The latter three silicon-containing products were formed in a ratio of ca. 3:2:3. Free, oligomeric silanes are also observed during coupling reactions with Cp*$_2$HfH$_2$ as catalyst. Presumably because of steric hindrance at the metal center, this hafnium hydride couples Si-H bonds very slowly. This allows observation by $^1$H NMR spectroscopy of conversion of PhSiH$_3$ to disilane, which is followed more slowly by appearance of trisilane and finally, tetrasilane. When heated to 120° C. for a day, the silane compounds are converted to higher molecular weight oligomers. These observations provide evidence for the stepwise nature of chain growth. Early in reaction of Cp*$_2$HfH$_2$ with PhH$_2$SiSiH$_2$Ph, significant quantities of PhSiH$_3$ are detected, establishing reversibility of Si-Si bond formation.

This catalytic cycle appears to represent a new polymerization mechanism, and is unusual as a coordination polymerization in that it involves step growth of polymer rather than chain growth. The mechanism accounts for the stringent steric requirements observed for catalysts and silane monomers, since the four-center transition states are inherently quite crowded.

EXAMPLE II

The following zirconium silyl derivatives appear to be the fastest catalysts studied thus far: Cp$_2$Zr[Si(SiMe$_3$)$_3$]SiMe$_3$, Cp$_2$Zr(SiMe$_3$)Me, Cp$_2$Zr[Si(SiMe$_3$)$_3$]Me, CpCp*M[Si(SiMe$_3$)$_3$]Me (M=Zr, Hf). In each case, the catalysts were tested by adding ca. 2 ml of monomer (PhSiH$_3$) to a toluene solution (ca. 2 ml) of the catalyst (ca. 0.6 mol %) under argon or nitrogen. These solutions were stirred for ca. 1 day, then passed through a florisil column. The column was then eluted with ca. 200 ml toluene. Removal of solvent and washing with pentane gives good yields of the colorless, brittle, glassy polysilane —(SiPhH)$_x$— (1.4-1.6 g). Additional polymerizations with benzyl silane and p-tolyl silane suggests that these polymerization reactions are quite general.

Thus the invention discloses that early transition-metal silyl compounds (metal-silicon bonded compounds where the metal is tatanium, zirconium, hafnium or tantalum) are efficient catalysts for the dehydrogenative coupling of silanes containing silicon-hydrogen bonds to silicon-silicon bonded oligomers and polymers, with degrees of polymerization ranging from 2 to approximately 70-85.

What is claimed is:

1. A method for catalytic dehydrogenative silane polymerization comprising, adding metal silyl catalyst precursors to silanes in a hydrocarbon solution to obtain polysilanes.

2. The method of claim 1 wherein said precursors are early transition metal silyl derivatives.

3. A method for catalytic dehydrogenative silane polymerization comprising, adding metal silyl catalyst precursors to silanes in a hydrocarbon solution, which precursors are silyl complexes of the type Cp'$_2$M(SiR$_3$)R', wherein Cp=$\eta^5$-C$_5$H$_5$, Cp'=Cp, Cp*, Cp* =$\eta^5$-C$_5$Me$_5$; Me=methyl; M=Zr, Hf: R=Me, Ph, SiMe$_3$ and R'=Cl, alkyl, silyl to obtain polysilanes.

4. The method of claim 3 wherein primary and secondary silanes are polymerized to polysilanes.

5. The method of claim 3 wherein said solution is selected from the group consisting of benzene, toluene, pentane or THF.

6. The method of claim 3 wherein said reaction is conducted between −78° to 150° C.

7. The method of claim 3 wherein said silanes include RSiH$_3$ and said polysilanes include H(SiHR)$_m$(SiHR)$_n$H and H(SiRR')$_n$H.

8. The method of claim 3 wherein such catalytic polymerization of silanes proceeds by the following mechanism:

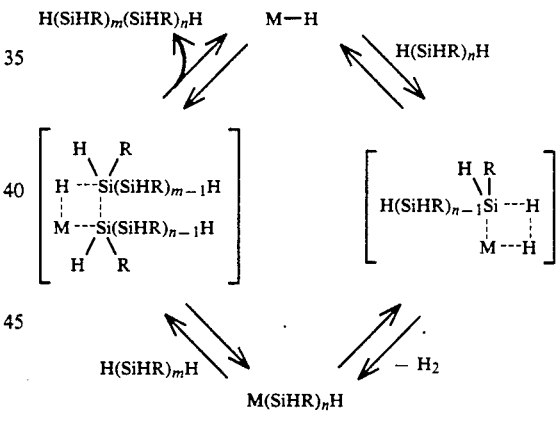

* * * * *